United States Patent
Koch (10) Patent No.: US 8,511,892 B2
(45) Date of Patent: Aug. 20, 2013

(54) DEVICE FOR MEASURING THE BODY CORE TEMPERATURE

(75) Inventor: Jochim Koch, Ratzeburg (DE)

(73) Assignee: Drägerwerk Aktiengesellschaft, Lübeck (DE)

( * ) Notice: Subject to any disclaimer, the term of this patent is extended or adjusted under 35 U.S.C. 154(b) by 1319 days.

(21) Appl. No.: 11/062,830

(22) Filed: Feb. 22, 2005

(65) Prior Publication Data
US 2005/0276309 A1 Dec. 15, 2005

(30) Foreign Application Priority Data
Jun. 11, 2004 (DE) .......................... 10 2004 028 359

(51) Int. Cl.
*G01K 1/02* (2006.01)
*G01K 1/14* (2006.01)
*G01K 1/16* (2006.01)
*G01D 11/30* (2006.01)

(52) U.S. Cl.
USPC ............. 374/163; 374/208; 374/44; 374/143; 374/198; 374/120; 600/474; 600/549; 73/866.5

(58) Field of Classification Search
USPC ................ 702/131, 139, 130; 374/208, 141, 374/163, 183, 100, 143, 120, 198; 600/474, 600/549; 116/216; 601/141; 607/4, 5, 96, 607/104, 106, 18, 112; 73/866.5
See application file for complete search history.

(56) References Cited

U.S. PATENT DOCUMENTS

| | | | |
|---|---|---|---|
| 3,830,224 A | | 8/1974 | Vanzetti et al. |
| 3,852,092 A | * | 12/1974 | Patterson et al. ............. 374/161 |
| 4,090,504 A | | 5/1978 | Nathan |
| 4,129,125 A | * | 12/1978 | Lester et al. ................... 600/484 |
| 4,135,497 A | * | 1/1979 | Meyers et al. ................. 600/549 |
| 4,412,546 A | * | 11/1983 | Barthels ......................... 600/522 |
| 4,434,801 A | * | 3/1984 | Jiminez et al. ................ 600/502 |
| 4,572,197 A | * | 2/1986 | Moore et al. ................... 600/389 |
| 4,576,179 A | * | 3/1986 | Manus et al. .................. 600/484 |
| 4,747,413 A | | 5/1988 | Bloch |
| 4,763,660 A | * | 8/1988 | Kroll et al. ..................... 600/391 |
| 4,928,690 A | * | 5/1990 | Heilman et al. .................. 607/4 |
| 4,952,033 A | * | 8/1990 | Davis ............................. 358/300 |
| 5,050,612 A | * | 9/1991 | Matsumura .................... 600/483 |

(Continued)

FOREIGN PATENT DOCUMENTS
DE 29910633 U1 10/1999
DE 199 27 686 A1 3/2001
(Continued)

OTHER PUBLICATIONS

A. Alzheimer and M. Lewandowsky, 1937, *Neurologie und Psychiatrie*, Z. Neurol. Psychiat., 159, 75-81.

*Primary Examiner* — Gail Verbitsky
(74) *Attorney, Agent, or Firm* — McGlew and Tuttle, P.C.

(57) ABSTRACT

A device for measuring the body core temperature of a person contains a structure for firmly wrapping around the upper body of the person. A double temperature sensor is connected with the structure for wrapping around the upper body such that the double temperature sensor is pressed elastically onto the upper body in the state in which it is put on in the area of the sternum. The device for measuring the body core temperature is suitable for the integration of a body core temperature measurement in clothing or chest belt systems.

27 Claims, 3 Drawing Sheets (56) References Cited

U.S. PATENT DOCUMENTS

| | | | |
|---|---|---|---|
| 5,816,706 A * | 10/1998 | Heikkila et al. | 374/134 |
| 5,830,136 A * | 11/1998 | Delonzor et al. | 600/323 |
| 6,024,575 A * | 2/2000 | Ulrich | 434/236 |
| 6,086,247 A * | 7/2000 | von Hollen | 374/137 |
| 6,102,856 A | 8/2000 | Groff et al. | |
| 6,183,422 B1 * | 2/2001 | Rytky et al. | 600/508 |
| 6,272,365 B1 | 8/2001 | Ronkainen et al. | |
| 6,287,262 B1 * | 9/2001 | Amano et al. | 600/500 |
| 6,292,685 B1 * | 9/2001 | Pompei | 600/474 |
| 6,418,394 B1 * | 7/2002 | Puolakanaho et al. | 702/139 |
| 6,436,038 B1 * | 8/2002 | Engstrom | 600/301 |
| 6,491,647 B1 * | 12/2002 | Bridger et al. | 600/585 |
| 6,595,929 B2 * | 7/2003 | Stivoric et al. | 600/549 |
| 6,842,722 B2 * | 1/2005 | David | 702/189 |
| 6,847,913 B2 * | 1/2005 | Wigley et al. | 702/131 |
| 6,963,772 B2 * | 11/2005 | Bloom et al. | 600/547 |
| 7,039,454 B1 * | 5/2006 | Kaga et al. | 600/476 |
| 7,051,120 B2 * | 5/2006 | Greene et al. | 709/250 |
| 7,059,767 B2 * | 6/2006 | Tokita et al. | 374/163 |
| 7,122,047 B2 * | 10/2006 | Grahn et al. | 607/108 |
| 2002/0013538 A1 * | 1/2002 | Teller | 600/549 |
| 2002/0138017 A1 * | 9/2002 | Bui et al. | 600/537 |
| 2003/0009087 A1 * | 1/2003 | Keirsbilck | 600/300 |
| 2003/0032893 A1 | 2/2003 | Koch | |
| 2003/0212319 A1 * | 11/2003 | Magill | 600/382 |
| 2004/0083526 A1 * | 5/2004 | Ichigaya | 2/2.14 |
| 2004/0158156 A1 * | 8/2004 | Schneemeyer et al. | 600/474 |
| 2004/0162587 A1 * | 8/2004 | Hampton et al. | 607/5 |
| 2004/0260167 A1 * | 12/2004 | Leonhardt et al. | 600/390 |
| 2005/0101843 A1 * | 5/2005 | Quinn et al. | 600/300 |
| 2005/0145191 A1 * | 7/2005 | Cohen et al. | 119/455 |
| 2005/0165323 A1 * | 7/2005 | Montgomery et al. | 600/544 |
| 2005/0259714 A1 * | 11/2005 | Lozinski | 374/29 |
| 2006/0047218 A1 * | 3/2006 | Bloom et al. | 600/547 |
| 2006/0084855 A1 * | 4/2006 | Teschner et al. | 600/390 |
| 2006/0106311 A1 * | 5/2006 | Lo et al. | 600/459 |
| 2008/0161715 A1 * | 7/2008 | Stivoric et al. | 600/549 |

FOREIGN PATENT DOCUMENTS

| | | |
|---|---|---|
| DE | 10038247 A1 * | 5/2001 |
| DE | 10038247 A2 | 5/2001 |
| DE | 100 05 526 A1 | 8/2001 |
| DE | 10005526 A1 | 8/2001 |
| DE | 20212110 U1 | 3/2003 |
| DE | 10139705 A1 | 4/2003 |
| EP | 0168604 A1 | 1/1986 |
| EP | GB 2 309 304 A | 7/1997 |
| GB | 1575426 | 9/1980 |
| GB | 2302176 | 1/1997 |
| GB | 2408105 | 5/2005 |
| RU | 2143220 C1 * | 12/1999 |

* cited by examiner

DEVICE FOR MEASURING THE BODY CORE TEMPERATURE

CROSS REFERENCE TO RELATED APPLICATIONS

This application claims the benefit of priority under 35 U.S.C. §119 of DE 10 2004 028 359.1 filed Jun. 11, 2004, the entire contents of which are incorporated herein by reference.

FIELD OF THE INVENTION

The present invention pertains to a device with double temperature sensor for measuring the body core temperature of a person.

BACKGROUND OF THE INVENTION

Such devices can be used wherever the body core temperature is to be determined, but inaccuracies due to conventional peripheral measuring methods are undesirable or cannot be tolerated. Devices according to the present invention are especially suitable for monitoring firemen and rescue personnel, who are exposed to physical strains at extreme temperatures. Strain limits can be set and mission decisions can be made with the data thus obtained.

Another field of use is represented by patient monitoring in medical applications. In particular, the monitoring of diseases associated with fever and patient monitoring after severe hypothermia can be effectively accomplished by monitoring the body core temperature.

Measuring or monitoring the body temperature as an important vital parameter has been known for a long time. The body core temperature is a highly informative parameter concerning vital functions of a subject. However, it cannot be readily determined by conventional temperature measuring methods. Temperature measurements at more or less peripheral measuring points show varying deviations of the measured temperature from the body core temperature. These deviations are either difficult to calculate, lead to poorly reproducible results or show highly sensitive dependences on various extraneous effects.

Various efforts have been made to reduce these effects by clever measuring set-ups. Thus, it is known that the temperature can be measured within the armpit or rectally in the case of the measurement of fever. What is most important in connection with the measurement in the armpit is to position the thermometer in a stable manner with the arm held in a constant position. This considerably restricts the freedom of movement, and this method is therefore inherently ruled out for the monitoring of active mission personnel. Rectal measurement may be dangerous when full freedom of movement is required at the same time. Even though the above-mentioned two possibilities represent a step towards measurement near the body, the measurement is still carried out at a relatively great distance from the core. In addition, both are ruled out for the monitoring of active mission personnel due to the restrictions associated with them in terms of the freedom of movement.

It is known that temperature sensors can be arranged in the armpit by means of holding mechanisms, which guarantees the freedom of movement of the arm (U.S. Pat. No. 4,747,413). However, these arrangements are suitable for monitoring fever only and have the drawback that the body temperature is measured at a relatively great distance from the core. It is known, furthermore, that the surface temperature of humans can be measured or monitored by placing various temperature sensors on the body surface (GB 2 309 304 A). However, this method likewise fails to open up a possibility of measuring the body core temperature. It is known that sensors used for temperature measurement can be arranged near the surface and that these sensors can be combined with sensors for monitoring other vital parameters (DE 199 27 686 A1). It is also known that temperature sensors arranged near the surface can be combined with means for determining the position of the wearer of these sensors (DE 100 05 526 A1). Integration of individual sensors in articles of clothing was proposed as well (DE 199 27 686 A1).

All these measuring set-ups are characterized by the shortcomings of a near-surface temperature measurement that were already mentioned above.

It is, furthermore, known that the heat flow through the body surface can be measured and the body core temperature can be inferred from this. Devices with double temperature sensors are especially suitable for measuring the heat flow through the body surface. Double temperature sensors in the sense of the present invention comprise essentially two temperature sensors, which are arranged at a fixed distance from one another in a holding construction such that one temperature sensor assumes a position near the body and is in contact with the skin, the second temperature sensor is arranged at a defined distance from the first temperature sensor in a position away from the body, and a defined heat flow takes place between the two sensors.

A very readily predictable, known or reproducible sensor thermal conductivity can be obtained for the material/medium in the space between the sensors due to a special embodiment of the holding construction. The thermal conductivity of a particular piece of material/medium is determined by the size and shape of the particular piece, and the specific thermal conductivity unit value or thermal conductivity constant for that specific material. When the particular piece of material/medium is the standard or size of one unit, the thermal conductivity is by definition equal to the thermal conductivity unit value or thermal conductivity constant for that specific material. The two values are often used interchangeably. If, in addition, the body tissue thermal conductivity of the tissue is determined, such as by estimation, between the body surface at the site of the sensor and the zone in which nearly the body core temperature prevails, the body core temperature can be extrapolated from the sensor and body tissue thermal conductivity, i.e., the estimated body tissue thermal conductivity of the tissue and the known sensor thermal conductivity of the material/medium between the double temperature sensor. The formula $$T_{core} = T_1 + (T_1 - T_2)/k_s/k_t$$

in which
$T_{core}$ is the body core temperature
$T_1$ is the temperature in at a position near the body
$T_2$ is the temperature in at a position away from the body
$K_s$ is the known sensor thermal conductivity of the material/medium between the double temperature sensor
$k_t$ is the estimated body tissue thermal conductivity constant of the tissue,
is a common calculation instruction. Depending on the concrete requirements due to special environmental conditions, other calculation instructions are applicable, but they do not change anything in the above-mentioned principle of measurement.

The thermal conductivity constant of human tissue depends significantly on the degree of blood flow. The use of a double temperature sensor presupposes stable thermal conditions with the most constant thermal conductivity possible.

This requires, on the one hand, tissue areas with low or uniform blood flow, which are located between the body surface and the body core zone to be measured. A second requirement imposed on the position of the double temperature sensor is that the thinnest possible fat layer or no fat layer shall be located between the sensor and the core zone to be measured, because the strong insulating action of fatty tissue may hinder such measurements of the body core temperature as a whole or make them inaccurate. It is therefore known that a double temperature sensor may be arranged at the head in the area of the top. This position meets the above-mentioned requirements. The double temperature sensor is attached, for example, by means of a head strap.

However, this placement may sometimes be associated with a considerable loss of wearing comfort. Placing the double temperature sensor in the head area is ruled out in other cases because of insufficient space.

U.S. Pat. No. 5,816,706 discloses a heat flow sensor, which comprises, in principle, two parallel double temperature sensors, which are provided for measuring a body temperature near the core. It is assumed in this process that the body tissue has no constant thermal conductivity because of the variable blood flow. Two parameters, namely, the current thermal conductivity constant, which depends on the blood flow, and then, by means of this value, the body core temperature near the core of the body, can be determined simultaneously by means of the process and the double arrangement of the heat flow sensor. This process and the sensor are, however, substantially more complicated than a simple double temperature sensor. An arrangement with a plurality of double temperature sensors is, moreover, substantially larger and displays reduced dynamics during temperature measurements because of its high heat capacity.

SUMMARY OF THE INVENTION

Thus, the object of the present invention is to provide a device that makes possible a simple, accurate and reproducible body core temperature measurement with a high level of wearing comfort and avoids the drawbacks of the above-mentioned state of the art.

According to the invention, a device is provided for measuring the body core temperature of a person, containing a means for firmly wrapping around the upper body. A double temperature sensor is connected with the means for wrapping around the upper body such that it is pressed elastically onto the upper body in the state in which it is put on in the area of the sternum.

The double temperature sensor may be connected with the means for wrapping around the upper body such that it is pressed elastically onto the upper body in the state in which it is put on in the area of the sternum between the xiphoid body and the xiphoid process. The double temperature sensor may be connected with the means for wrapping around the upper body such that when it is put on in the area of the sternum, it is pressed on in a position that is described by an L:X ratio that is between 5.2 and 5.6, in which L is the height of the person and X is the distance from the level of the collar to the position of the double temperature sensor.

The means firmly wrapping around the upper body may be an elastic belt or an elastic article of clothing. The double temperature sensor may be fastened with a fastening means of variable extension to the means for firmly wrapping around the upper body such that the distance between the double temperature sensor and the means for wrapping around the upper body is variable. The fastening element may comprise a spring element, an elastic shaped part, a gel pad or a cushion that can be filled with a gas.

The elastic components may be designed such that the pressing pressure with which the double temperature sensor is pressed onto the body is at least $0.5$ $N/cm^2$. The elastic components may be designed such that the pressing pressure with which the double temperature sensor is pressed onto the body is at least $1.0$ $N/cm^2$. A means for measuring the pressing pressure with which the double temperature sensor is pressed onto the body may be present. The fastening element may comprises means for setting the pressing pressure with which the double temperature sensor is pressed onto the body.

Additional sensors for measuring body functions may be integrated into the device. Sensors for measuring the heart rate may be integrated into the means for wrapping around the upper body. A means for determining the wearer's position may be integrated into the device. An evaluating unit may be present for evaluating the sensor signals. A means for wireless data transmission from the evaluating unit to a receiving station may be employed. Electric lines for signal or data transmission may be integrated at least partly in the means for wrapping around the upper body.

Internal studies have shown that a double temperature sensor should not lie directly on a blood vessel, because the thermal conductivity constant of the tissue will thus depend on a vasomotricity and consequently the blood flow.

It is now assumed in the present invention that it is possible to arrange a double temperature sensor in a position that makes it possible to obtain similarly good or better measurement results compared to an arrangement at the head and avoids the drawbacks of arrangement in the area of the head. Anatomic considerations concerning the blood vessels in the area of the head show that these blood vessels assume very small diameters on the median vertical axis of symmetry of the human body. This is due to the fact that they essentially converge mutually toward one another from both outer sides of the body toward the axis of symmetry and terminate there. This applies to both the area of the head and the thoracic region. Small blood vessels with small diameters do not have a great effect on the heat flow in the radial direction through the body tissue. These areas are therefore suitable for the measurement of the body core temperature by means of a double temperature sensor, because it can be assumed that the thermal conductivity constant of the tissue is nearly constant here, which is in turn a prerequisite for a reliable body core temperature measurement.

Anatomic analyses of the chest show that there is a region near the heart that is located on the axis of symmetry of the body and is superimposed by fatty tissue only in highly adipose persons. By contrast, this region is covered by a low-fat skin tissue in athletically active persons and persons who are physically active. This region approximately corresponds to the position of the breastbone or sternum. A double temperature sensor can be positioned according to the present invention on the sternum in good contact with the skin. The especially advantageous anatomic region is located between the xiphoid body and the xiphoid process.

Thus, the present invention is embodied by a device for measuring the body core temperature of a person, containing a means for firmly wrapping around the upper body, characterized in that a double temperature sensor is connected with the means for wrapping around the upper body such that it is elastically pressed onto the upper body when it is placed in the area of the sternum.

Such a device according to the present invention makes do with an individual double temperature sensor, and it can consequently be manufactured substantially more simply and at a substantially lower cost, it can be handled more simply and has a greatly increased dynamics compared to devices with a plurality of double temperature sensors because of its low heat capacity.

A problem overcome by the present invention has been so far the special anatomy of the human body in the area of the sternum. In nearly all people, the area of interest for the measurement of the body core temperature over the sternum is located in a depression between the pectoral muscles. It is therefore not easy to apply a defined pressing pressure to this area by a simple tight cover or conventional means for wrapping around the upper body. The means used most commonly for wrapping around the upper body are chest belts, belt systems or tightly seated particles of clothing with at least partially elastic properties, and reference will be made below on several occasions to chest belts only for the explanation of the present invention, without excluding equivalent means. The reference comprises textile materials in the broad sense the word.

The distance between the sternum and the chest belt, which is due to the anatomic conditions, can be filled out in many cases according to the present invention by the double temperature sensor thanks to an adapted dimensioning of the double temperature sensor, as a result of which the controlled pressing-on of the double temperature sensor is made possible in the area of the sternum.

The double temperature sensor is advantageously fastened with a fastening element of variable extension to the means for wrapping firmly around the upper body such that the distance between the double temperature sensor and the means for wrapping around the upper body is variable. This makes possible the use of the invention even on upper bodies whose anatomy causes greater distances between the sternum and the chest belt. The fastening element increases the distance between the chest belt and the double temperature sensor. If the distance is set such that it will be somewhat greater because of the fastening element than it is required by the shape of the upper body in order to bring the double temperature sensor in contact with the skin, the chest belt is slightly raised. As a result, an elastic restoring forces is generated, which is transmitted by the fastening element to the double temperature sensor and leads to the double temperature sensor being pressed onto the upper body in the area of the sternum. Depending on the fastening means used, this can contribute more or less to the generation of the elastic restoring force, i.e., it will be deformed to different extents under the action of pressure. It may be advantageous to include this deformation of the fastening element in the calculation of mechanical requirements that are to be imposed on the wrapping-around means.

Fastening means that have a spring element, elastic shaped parts, air cushion film, other air-filled elastic shaped elements, gel pads or similar objects may be advantageously used. It may also be advantageous to use a fastening element that makes it possible to set the pressing pressure of the double temperature sensor. Hollow structures filled with gas, i.e., cushions, are especially suitable for this. Air is sufficient as a gas filling in most cases. A variably fillable cushion, in particular, offers additionally the advantage of comfortable adaptability of the pressing pressure of the double temperature sensor during a mission. Should the double temperature sensor send signals that do not appear to be plausible, it is possible, for example, to briefly release the sensor in order to press it again onto the upper body shortly thereafter. All applications with changing requirements on the pressing pressure of the double temperature sensor can also be embodied with such a cushion as the fastening means. It proved to be advantageous to design the elastic components of a device according to the present invention such that the pressing pressure with which the double temperature sensor is pressed onto the body is at least 0.5 N/cm$^2$. An especially high quality of measurement of the body core temperature can be achieved if the elastic component is designed such that the pressing pressure with which the double temperature sensor is pressed onto the body is at least 1.0 N/cm$^2$. Means for measuring the pressing pressure with which the double temperature sensor is pressed onto the body may be present in an advantageous embodiment of the present invention.

The combination of the double temperature sensor, the fastening element and the means for wrapping around the upper body leads to numerous possibilities of combining the measurement of the body core temperature with the measurement of other vital parameters. Furthermore, means for supporting the determination of the wearer's position can be integrated without problems. Devices according to the present invention are especially predestined for the combined measurement of the body core temperature and the heart rate, which makes possible the effective determination of various strain indices. Since conventional chest belts for measuring the heart rate are usually equipped with sensors or electrodes, which are in contact with the upper body on the side, a double temperature sensor can be fastened to such a belt in the manner according to the present invention in the area of the sternum without the positions of the sensors for measuring the heart rate having to be changed. It must only be ensured that the pressing pressure generated at the double temperature sensor will not be so strong that the chest belt will lift off from the sternum excessively and the measurement of the heart rate will be excessively hindered as a result. This can be guaranteed by a corresponding dimensioning of the fastening elements according to the present invention.

An evaluating unit for evaluating the signals of the double temperature sensor and/or other sensors may be advantageously integrated in a device according to the present invention. The double temperature sensor can thus be coupled directly with an evaluating unit. It is especially advantageous if means for a wireless data transmission from the evaluating unit to a receiving station are present.

Sensors, evaluating units and means for data transmission are advantageously arranged in different positions in other advantageous embodiments of devices according to the present invention and are connected with one another by electric lines for signal or data transmission.

Wired and wireless transmission means may be advantageously combined with one another.

It is especially advantageous if electric lines for signal or data transmission are integrated at least partly in the means for wrapping around the upper body. This leads to an increase in the reliability of operation and the wearing comfort because error-prone cables can partly be eliminated.

Exact placement especially of the double temperature sensor is necessary for the high reliability of devices according to the present invention. The connection with the means for wrapping firmly around the upper body offers good conditions for this. In case of a chest belt, this can be positioned in a simple manner. It will subsequently maintain its position unless stronger forces act on it. As a result, the double temperature sensor will also maintain its exact position.

The use of elastic articles of clothing as means for firmly wrapping around the upper body offers an even greater safety in positioning the double temperature sensor. The fit of a fitting article of clothing can be described and predicted relatively accurately on the basis of conventional sizes. An elastic article of clothing of the correct size changes its position relative to the wearer's body only minimally at best during wear. Consequently the connection of a double temperature sensor with an elastic article of clothing offers a high level of stability of position. This stability of the position can also be utilized according to the present invention in the area over the sternum.

Large amounts of anthropometric data of different body types were evaluated in setting up the so-called metric index (Strömgen H.: On Anthropometric Indices for Distinguishing Body types. *Z. Neurol. Psychiat.*, 159, 75-81 (1937)). The breadth of the shoulders, the breadth of the chest, and the depth of the breast were measured, among other things. Different positions on the body surface can be described on the basis of these data by coordinate-like parameters, which also applies, of course, to preferred positions for arranging a double temperature sensor. It is consequently especially advantageous if the double temperature sensor is connected with the means for wrapping around the upper body such that when it is placed in the area of the sternum, it is pressed on in a position that is described by an L:X ratio that is between 5.2 and 5.6, where L is the height of the person and X is the distance from the level of the collar to the position of the double temperature sensor.

The present invention will be explained in greater detail on the basis of two exemplary embodiments. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
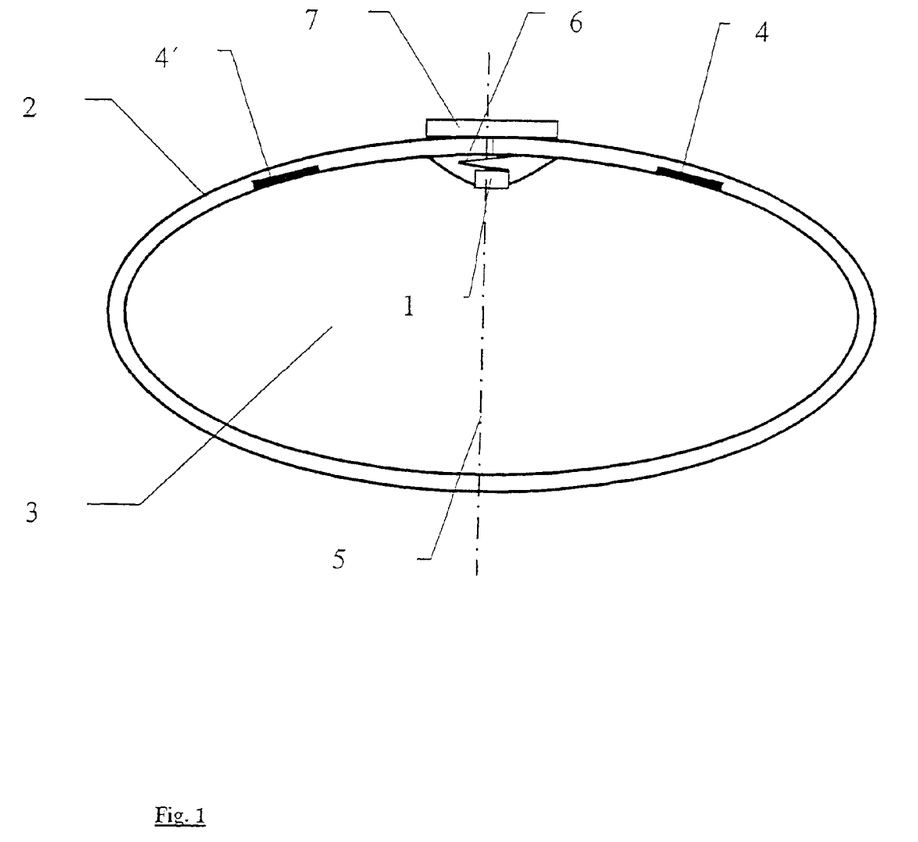
FIG. 1 is a schematic sectional view of a human upper body with a belt according to the present invention placed on with a double temperature sensor.

Referring to the drawings in particular, FIG. 1 illustrates the arrangement according to the present invention of a double temperature sensor 1 on a chest belt 2. The chest belt 2 is tightened around the upper body 3 of a person. In the terminology of the present invention, it is a means for wrapping firmly around the upper body. The level of the chest belt 2 is set by the user such that it is placed somewhat below the chest, but it still lies fully over the ribs. Two electrodes 4, 4' acting as sensors for measuring the pulse rate are placed on the chest belt. These are placed symmetrically on both sides laterally from the center line 5 of the body. With a fastening element, which comprises essentially a spring 6, the double temperature sensor 1 is fastened to the chest belt 2 in the middle between the two electrodes 4, 4', which act as pulse sensors. The double temperature sensor 1 is pressed by the spring 6 firmly onto the upper body 3, even though there is a rather great distance between the body surface and the chest belt 2 in its position. The spring 6 guarantees a pressing force of about 6 N to 10 N, which corresponds to a pressing pressure of 1 N/cm$^2$ to 1.5 N/cm$^2$ in the case of the double temperature sensor 1 used. As a result, there is a good heat transfer between the double temperature sensor 1 and the human tissue, which is a prerequisite for the accurate determination of the wearer's body core temperature. The tension of the chest belt 2 secures the sensors against slipping and thus prevents incorrect measurements. The sensors are fastened to the chest belt 2 such that they are arranged automatically in the body position suitable for the particular measurement if the chest belt 2 is placed correctly. The signals sent by the double temperature sensor 1 and the pulse sensors 4, 4' are processed in an evaluating unit 7 arranged on the outer side of the chest belt 2 and sent through cables (not shown) integrated in the chest belt 2 to a transmitting unit (not shown), from which they are sent in a cableless (e.g., wireless) manner to a receiving station (not shown). As an alternative, the transmitting unit may be integrated in the evaluating unit 7. A monitoring unit (not shown) for displaying the measured vital parameters as well as another evaluation of the received data are connected with the receiving station. Calculation routines permit the continuous monitoring of the physiological strain (e.g., according to the model of Moran et al., presented in Moran, D. S., A. Shizer, K. B. Pandolf: A Physiological Strain Index to Evaluate Heat Stress. *A. J. Physiol.*, 275 (Regul. Integr. Comp. Physiol., 44): R129-R134, 1998).

Figure 2:
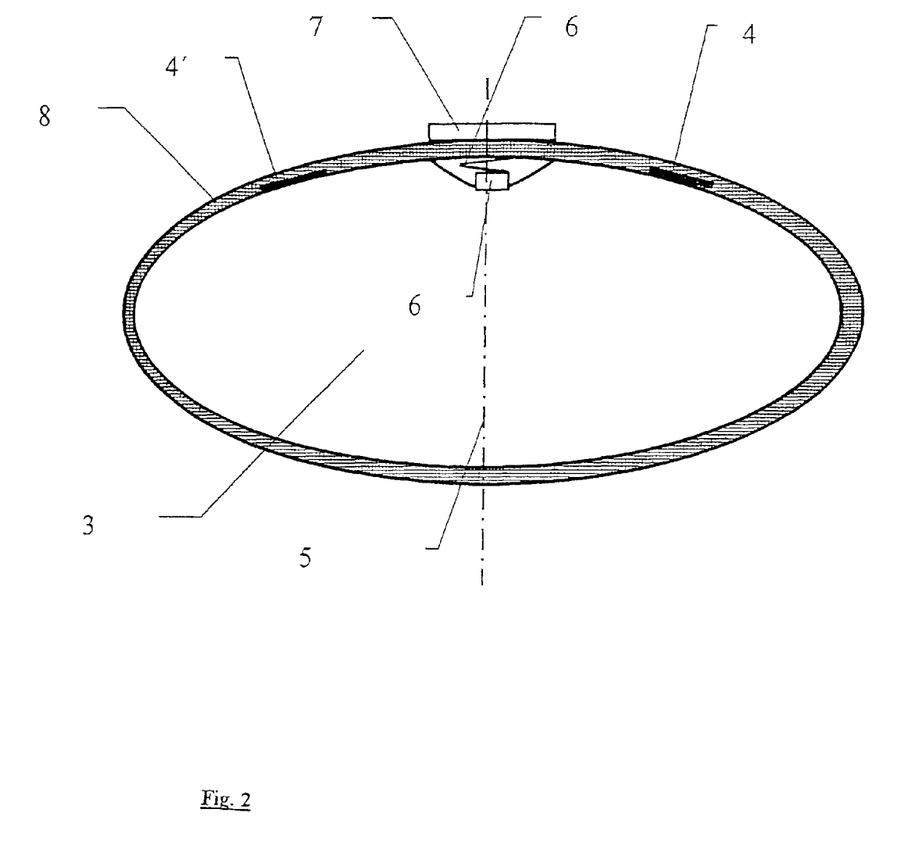
FIG. 2 is a schematic sectional view of a human upper body with an elastic article of clothing placed on with a double temperature sensor.

Contrary to FIG. 1, FIG. 2 shows an embodiment of a device according to the present invention in which electrodes 4, 4' for measuring the heart rate and a double temperature sensor 1 are connected with an elastic article of clothing 8. The two electrodes 4, 4' are integrated in the article of clothing 8. The double temperature sensor 1 is fastened in the above-described manner to the inner side of the article of clothing 8 with a fastening element, which comprises essentially a spring 6. The article of clothing 8 is elastic and has a circumference in the untightened state that is smaller than the circumference of the upper body 3. As a result, it is in close contact with convex areas of the wearer's upper body 3 during wear. It forms a tight elastic cover without contact with the skin over concave areas of the upper body 3. The fastening element with the spring 6 is supported over the sternum against such a tight area and presses the double temperature sensor 1 against the upper body 3 in the area of the sternum. The embodiment of the device according to the present invention as an article of clothing makes possible the especially accurate arrangement of the sensors. In case of the combination of a double temperature sensor with electrodes for pulse measurement, which are arranged to the side of the sternum, it is possible to position the article of clothing and consequently also the double temperature sensor highly accurately by slightly displacing the article of clothing by controlling the presence of a pulse signal.

Due to the elastic article of clothing fitting tightly, there also is a high level of safety against slipping and there is good acceptance by the mission personnel because of a corresponding wearing comfort, since an article of clothing thus equipped can be used without problems as part of a protective clothing, which has to be put on anyway. The signals sent by the double temperature sensor 1 and the pulse sensors 4, 4' are processed in an evaluating unit 7 arranged on the outer side of the article of clothing 8 in this exemplary embodiment as well, and they are sent through cables (not shown) integrated within the article of clothing 8 to a transmitting unit (not shown), from which they are transmitted to a receiving station (not shown) without cables. A monitoring unit (not shown) for displaying measured vital parameters as well as for a further processing of the received data is connected with the receiving station. Calculation routines make possible the continuous monitoring of the physiological strain in this case as well.

Figure 3:
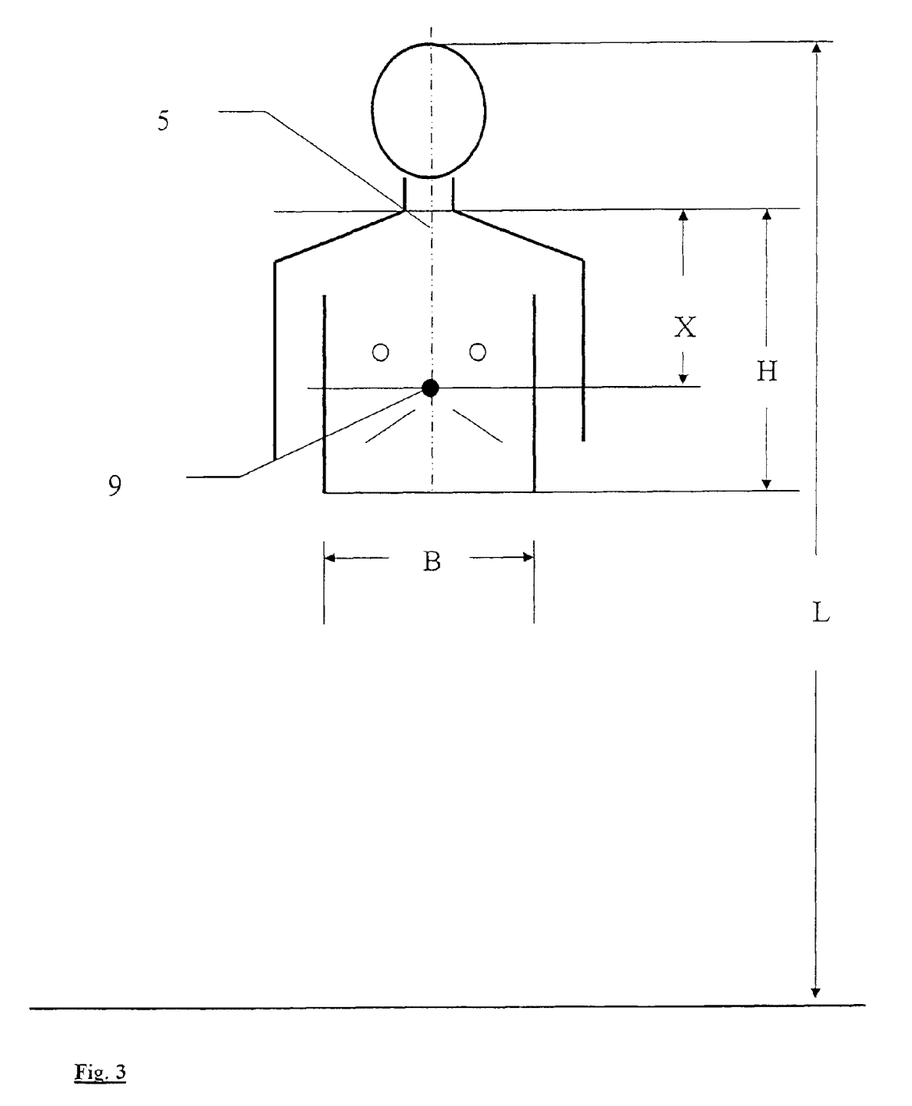
FIG. 3 is a schematic view of a human upper body for describing anthropometric measurement points.

FIG. 3 schematically shows the view of an upper body. The level H describes the distance between the hips and the shoulders at the level of the collar. This is a measure that is significant for the clothing industry. Other measures, which are used for setting the sizes, are the overall length L and the breadth B of the body. The variable X describes the vertical distance from the level of the collar or the base of the neck. If it is related to the overall length, a position on the central axis 5 of a person can be described highly accurately and in relation to off-the-rack clothing. It was found that good results can be obtained by the measurement of the body core temperature with a double temperature sensor if the double temperature sensor is connected with the article of clothing such that when it is put on in the area of the sternum, it is pressed on in a position that is described by an L:X ratio that is between 5.2 and 5.6.

While specific embodiments of the invention have been shown and described in detail to illustrate the application of the principles of the invention, it will be understood that the invention may be embodied otherwise without departing from such principles.

What is claimed is:

1. A device for measuring the body core temperature of a person, the device comprising
 a means for firmly wrapping around the upper body of the person;
 a double temperature sensor connected with said means for wrapping around the upper body such that it is pressed elastically onto the upper body in the state in which it is put on in the area of the sternum of the person, said double temperature sensor including first and second temperature sensors arranged spaced from one another by a known thermal conductivity, said first temperature sensor being arranged against the area of the sternum, said second temperature sensor being arranged in combination with said first temperature sensor and said thermal conductivity to measure heat flow through the area of the sternum, the double temperature sensor being fastened with a fastening means of variable extension to the means for firmly wrapping around the upper body such that the distance between the double temperature sensor and the means for wrapping around the upper body is variable.

2. A device in accordance with claim 1, wherein the double temperature sensor is connected with the means for wrapping around the upper body such that it is pressed elastically onto the upper body in the state in which it is put on in the area of the sternum between the xiphoid body and the xiphoid process.

3. A device in accordance with claim 1, wherein the double temperature sensor is connected with the means for wrapping around the upper body such that when it is put on in the area of the sternum, it is pressed on in a position and the position is described by an L:X ratio that is between 5.2 and 5.6, in which L is the height of the person and X is the distance from a level a base of the neck of the person to the position of the double temperature sensor.

4. A device in accordance with claim 1, wherein the means firmly wrapping around the upper body is an elastic belt.

5. A device in accordance with claim 1, wherein the means for firmly wrapping around the upper body is an elastic article of clothing.

6. A device in accordance with claim 1, wherein the fastening means comprises a spring element.

7. A device in accordance with claim 1, wherein the fastening means comprises an elastic shaped part.

8. A device in accordance with claim 1, wherein the fastening means comprises a gel pad.

9. A device in accordance with claim 1, wherein the fastening means comprises a cushion that can be filled with a gas.

10. A device in accordance with claim 1, wherein: a biasing element biases said double temperature sensor onto the body with a pressure of at least 0.5 N/cm$^2$.

11. A device in accordance with claim 1, wherein: a biasing element biases said double temperature sensor onto the body with a pressure of at least 1.0 N/cm$^2$.

12. A device in accordance with claim 1, further comprising: means for measuring the pressing pressure with which the double temperature sensor is pressed onto the body.

13. A device in accordance with claim 12, further comprising: means for setting a pressing pressure with which the double temperature sensor is pressed onto the body.

14. A device in accordance with claim 1, further comprising additional sensors for measuring body functions, said sensors being integrated into the device.

15. A device in accordance with claim 14, said additional sensors comprise sensors for measuring the heart rate, said sensors being integrated into the means for wrapping around the upper body.

16. A device in accordance with claim 1, further comprising means for determining the wearer's position, said means for determining the wearer's position being integrated into the device.

17. A device in accordance with claim 1, further comprising an evaluating unit receiving signals from said first and second temperature sensors, said evaluating unit using said known thermal conductivity between said first and second sensors, and using said signals from said first and second sensors to determine a heat flow through the area of the sternum, said evaluating unit using said heat flow and an estimate of a thermal conductivity of body tissue in the area of the sternum to determine the core body temperature of the person.

18. A device in accordance with claim 17, further comprising a receiving station and means for wireless data transmission from the evaluating unit to a receiving station.

19. A device in accordance with claim 1, wherein electric lines for signal or data transmission are integrated at least partly in the means for wrapping around the upper body.

20. A device for measuring the body core temperature of a person, the device comprising:
 a belt firmly wrappable around an upper body of the person;
 a double temperature sensor connected to said belt, said double temperature sensor including first and second temperature sensors arranged spaced from one another by a material having a predetermined thermal conductivity determined based on size and shape, said first temperature sensor being arranged against an area of a sternum of the person, said second temperature sensor being arranged in combination with said first temperature sensor and said material having said predetermined thermal conductivity to measure heat flow through the area of the sternum;
 a biasing element connecting said double temperature sensor to said belt, said biasing element and said belt being arranged to bias said double sensor against the area of the sternum of the person when said belt is wrapped around the upper body of the person;
 an evaluating unit receiving signals from said first and second temperature sensors, said evaluating unit using said predetermined thermal conductivity between said first and second sensors, and using said signals from said first and second sensors to determine a heat flow through the area of the sternum, said evaluating unit using said heat flow and an estimate of a thermal conductivity of body tissue in the area of the sternum to determine the body core temperature of the person.

21. A device in accordance with claim 20, wherein:
said first temperature sensor is arranged in contact with skin of the person, said second temperature sensor is arranged at a specific fixed distance from said first temperature sensor at a position away from the body with a defined heat flow taking place between said first and second temperature sensors.

22. A device in accordance with claim 20, wherein:
said biasing element biases said double sensor over the sternum in a depression between pectoral muscles of the person.

23. A device in accordance with claim 22, wherein:
said belt bridges across the depression between the pectoral muscles.

24. A device in accordance with claim 20, wherein:
said biasing element has a variable extension.

25. A device in accordance with claim 20, wherein:
said biasing element biases said double temperature sensor on to the sternum with a pressure equal to or greater than $0.5 \text{ N/cm}^2$.

26. A method for measuring body core temperature of a person, the method comprising the steps of:
wrapping a belt firmly around an upper body of the person;
providing a double temperature sensor arranged on said belt, said double temperature sensor including first and second temperature sensors arranged space from one another by a material having a predetermined thermal conductivity determined based on size and shape;
arranging said first temperature sensor against an area of the sternum of the person;
arranging said second temperature sensor in combination with said first temperature sensor and said material having said predetermined thermal conductivity to measure heat flow through the area of the sternum;
biasing said double temperature sensor against the area of the sternum of the person;
determining a heat flow through the area of the sternum from said predetermined thermal conductivity and signals from said first and second temperature sensors;
determining the body core temperature of the person from said heat flow and an estimate of a thermal conductivity of body tissue in the area of the sternum of the person.

27. A device for measuring the body core temperature of a person, the device comprising
a means for firmly wrapping around the upper body of the person;
a double temperature sensor connected with said means for wrapping around the upper body such that it is pressed elastically onto the upper body in the state in which it is put on in the area of the sternum of the person, said double temperature sensor including first and second temperature sensors arranged spaced from one another by a known thermal conductivity, said first temperature sensor being arranged against the area of the sternum, said second temperature sensor being arranged in combination with said first temperature sensor and said thermal conductivity to measure heat flow through the area of the sternum;
means for measuring the pressing pressure with which the double temperature sensor is pressed onto the body.

\* \* \* \* \*